United States Patent
Naranjo et al.

(10) Patent No.: US 12,101,688 B2
(45) Date of Patent: Sep. 24, 2024

(54) SYSTEM AND METHODS FOR PASSIVE CONTACT TRACING

(71) Applicant: Wells Fargo Bank, N.A., San Francisco, CA (US)

(72) Inventors: Paulo Ramon Naranjo, San Francisco, CA (US); Dominik Vitavsky, Belmont, CA (US)

(73) Assignee: Wells Fargo Bank, N.A., San Francisco, CA (US)

( * ) Notice: Subject to any disclaimer, the term of this patent is extended or adjusted under 35 U.S.C. 154(b) by 0 days.

(21) Appl. No.: 18/475,900

(22) Filed: Sep. 27, 2023

(65) Prior Publication Data
US 2024/0022872 A1    Jan. 18, 2024

Related U.S. Application Data

(62) Division of application No. 16/952,273, filed on Nov. 19, 2020, now Pat. No. 11,818,624.

(51) Int. Cl.
*H04W 4/02* (2018.01)
*G16H 50/80* (2018.01)
(Continued)

(52) U.S. Cl.
CPC ............ *H04W 4/023* (2013.01); *G16H 50/80* (2018.01); *H04L 43/50* (2013.01); *H04W 4/029* (2018.02); *H04W 12/69* (2021.01)

(58) Field of Classification Search
CPC ..... H04W 4/023; H04W 4/029; H04W 12/69; G16H 50/80; G16H 50/30; G16H 50/20;
(Continued)

(56) References Cited

U.S. PATENT DOCUMENTS

| 7,158,776 B1 | 1/2007 | Estes |
| 7,349,808 B1 | 3/2008 | Kreiswirth |

(Continued)

FOREIGN PATENT DOCUMENTS

WO    2010099488 A1    9/2010

OTHER PUBLICATIONS

Trivedi, Amee et al. "WifiTrace: Network-based Contact Tracing for Infectious Diseases Using Passive Wifi Sensing". Google Scholar, dated May 26, 2020.

*Primary Examiner* — Umair Ahsan
(74) *Attorney, Agent, or Firm* — K&L Gates LLP

(57) ABSTRACT

A method, apparatus, and computer program product for passive contact tracing is provided. An example method includes detecting a wireless signal from a mobile device at a sniffer device, generating a unique mobile device ID for said mobile device, recording the mobile device ID, identification data of the sniffer device, and a detection time, receiving a query for a target mobile device ID, proximate distance, and time period, and generating a list comprising a mobile device ID of every mobile device that came within the proximate distance of the target mobile device within the time period. The method further includes associating a mobile device with an employee by detecting an indication of employee identity within the range of a sniffer device and storing one or more mobile device IDs detected by said sniffer device as an employee parameter in an employee database.

20 Claims, 7 Drawing Sheets

(51) Int. Cl.
*H04L 43/50* (2022.01)
*H04W 4/029* (2018.01)
*H04W 12/69* (2021.01)

(58) Field of Classification Search
CPC ........ G16H 70/60; G16H 10/60; H04L 43/50; G06F 16/22
See application file for complete search history.

(56) References Cited

U.S. PATENT DOCUMENTS

| | | |
|---|---|---|
| 7,908,155 B2 | 3/2011 | Fuerst |
| 8,645,538 B2 | 2/2014 | Pan |
| 10,019,887 B1 | 7/2018 | Lejeune, Jr. |
| 10,251,610 B2 | 4/2019 | Parthasarathy |
| 2006/0036619 A1 | 2/2006 | Fuerst |
| 2013/0275160 A1* | 10/2013 | Lev .................. H04M 3/42357 705/3 |
| 2014/0167917 A2* | 6/2014 | Wallace ................. G16H 40/67 340/10.1 |
| 2015/0234981 A1 | 8/2015 | Naidich |
| 2016/0063209 A1 | 3/2016 | Malaviya |
| 2017/0024531 A1 | 1/2017 | Malaviya |
| 2017/0206334 A1 | 7/2017 | Huang |
| 2018/0052970 A1 | 2/2018 | Boss |
| 2018/0366221 A1 | 12/2018 | Crehore |
| 2019/0343429 A1 | 11/2019 | Elhawary |
| 2020/0004746 A1 | 1/2020 | Randall |
| 2020/0176125 A1 | 6/2020 | Chatterjea |
| 2021/0027592 A1 | 1/2021 | Shannon |
| 2021/0313074 A1* | 10/2021 | Mesirow ............... H04W 4/029 |
| 2021/0390807 A1 | 12/2021 | Chaurasia |

\* cited by examiner

SYSTEM AND METHODS FOR PASSIVE CONTACT TRACING

CROSS-REFERENCE TO RELATED APPLICATIONS

This application is a divisional of U.S. patent application Ser. No. 16/952,273, filed Nov. 19, 2020, the entire contents of which are incorporated herein by reference.

TECHNOLOGICAL FIELD

Example embodiments of the present disclosure relate generally to contact tracing and more particularly, to contact tracing in a workplace.

BACKGROUND

Places of work, such as office buildings, may have any number of employees present in the building at any given time. If an employee becomes ill, there is an associated risk of disease transmission to other employees in the same building. This is particularly worrisome in cases where the disease is highly contagious, or the associated pathogen is considered dangerous.

Conventional forms of contact tracing exist on the client side and require downloading an associated app on a mobile device. Typically, a mobile device may use Bluetooth to transmit a unique identifier to other surrounding mobile devices, sometimes by forming ad-hoc networks. However, if a user has not downloaded the app, the mobile device will not be visible to other phones, even if the user is within a detectable proximity.

BRIEF SUMMARY

In general, embodiments of the present disclosure provided herein provide improved methods of passive contact tracing. Other implementations for passive contact tracing will be, or will become, apparent to one with skill in the art upon examination of the following figures and detailed description. It is intended that all such additional implementations be included within this description be within the scope of the disclosure and be protected by the following claims.

Systems, apparatuses, methods, and computer program products are disclosed herein for improved methods of passive contact tracing. In one embodiment, with reference to the claimed method, a method for improved passive contact tracing is provided. The method may include detecting, at a sniffer device of one or more sniffer devices, a first wireless signal from a first mobile device, the first wireless signal comprising first mobile device identification data. The method may further include generating, via a device ID circuitry, a unique mobile device ID associated with the first mobile device identification data. The method may further include recording a set of data comprising the unique mobile device ID, identification data of the sniffer device that detected the first wireless signal, and a detection time at which the first wireless signal was detected. The method may further include storing said data in a mobile device location database. The method may further include receiving a query, via a location circuitry, the query comprising a target mobile device ID, a proximate distance, and a time period. The method may further include accessing the mobile device location database. The method may further include generating a list comprising a mobile device ID of every mobile device that came within the proximate distance to the target mobile device within the time period.

In some embodiments, the method may further include determining, via the location circuitry, the location of a mobile device using co-detections from one or more additional sniffer devices.

In some embodiments, the method may further include detecting an indication of employee identity, via an employee identification circuitry, within the range of the sniffer device and storing the detected mobile device ID as an employee parameter for the identified employee in the employee database. In such an embodiment, an indication of employee identity may comprise receiving an employee badge number, pin code, password, or biometric data stored in an employee database.

In some embodiments, the method further includes, detecting at a first sniffer device positioned at an entrance point, wireless signals from a plurality of mobile devices. The method further includes detecting, at a badge-in terminal, the identity of an employee via an employee identification circuitry. The method further includes storing the plurality of mobile device ID's as employee parameters for the identified employee in the employee database. The method further includes detecting an indication of employee identity, via the employee identification circuitry, near a subsequent sniffer device. The method further includes detecting one or more wireless signals comprising identification data from one or more mobile devices at the subsequent sniffer device. The method further includes updating the employee parameters for the identified employee in the employee database to add, delete, or otherwise modify associated mobile device ID's based on the detection of mobile devices at the subsequent sniffer device.

In some embodiments, the method further includes receiving a query request, via the location circuitry, comprising an employee identifier. The method further includes in response to receiving the query request, accessing an employee database. The method further includes identifying at least one mobile device ID associated with the employee from the employee database. The method further includes generating a query for the at least one mobile device ID associated with the employee from the database.

In some embodiments, the proximate distance is a configurable parameter and is based at least in part, on an associated pathogen. In some embodiments, the time period is a configurable parameter and is based at least in part, on an associated pathogen.

In some embodiments, the method further includes recording, via a thermometer monitor, a temperature of an employee and generating, via a sickness detection circuitry, in response to detecting an employee having a temperature above a threshold temperature, an alert. In some other embodiments, the method includes recording, via at least one microphone, surrounding auditory stimuli and generating, via a sickness detection circuitry, in response to detecting auditory stimuli indicative of an illness, an alert.

In some embodiments, the method further includes determining the one or more employees associated with a mobile device ID of the identified mobile devices that came within the proximate distance to the target mobile device within the time period and notifying the one or more employees, via a notification, they may have come in contact with an illness. In some embodiments, the notification comprises an SMS message, email, or management intervention.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings. The components illustrated in the figures may or may not be present in certain embodiments described herein. Some embodiments may include fewer (or more) components than those shown in the figures.

DETAILED DESCRIPTION

Figure 1:
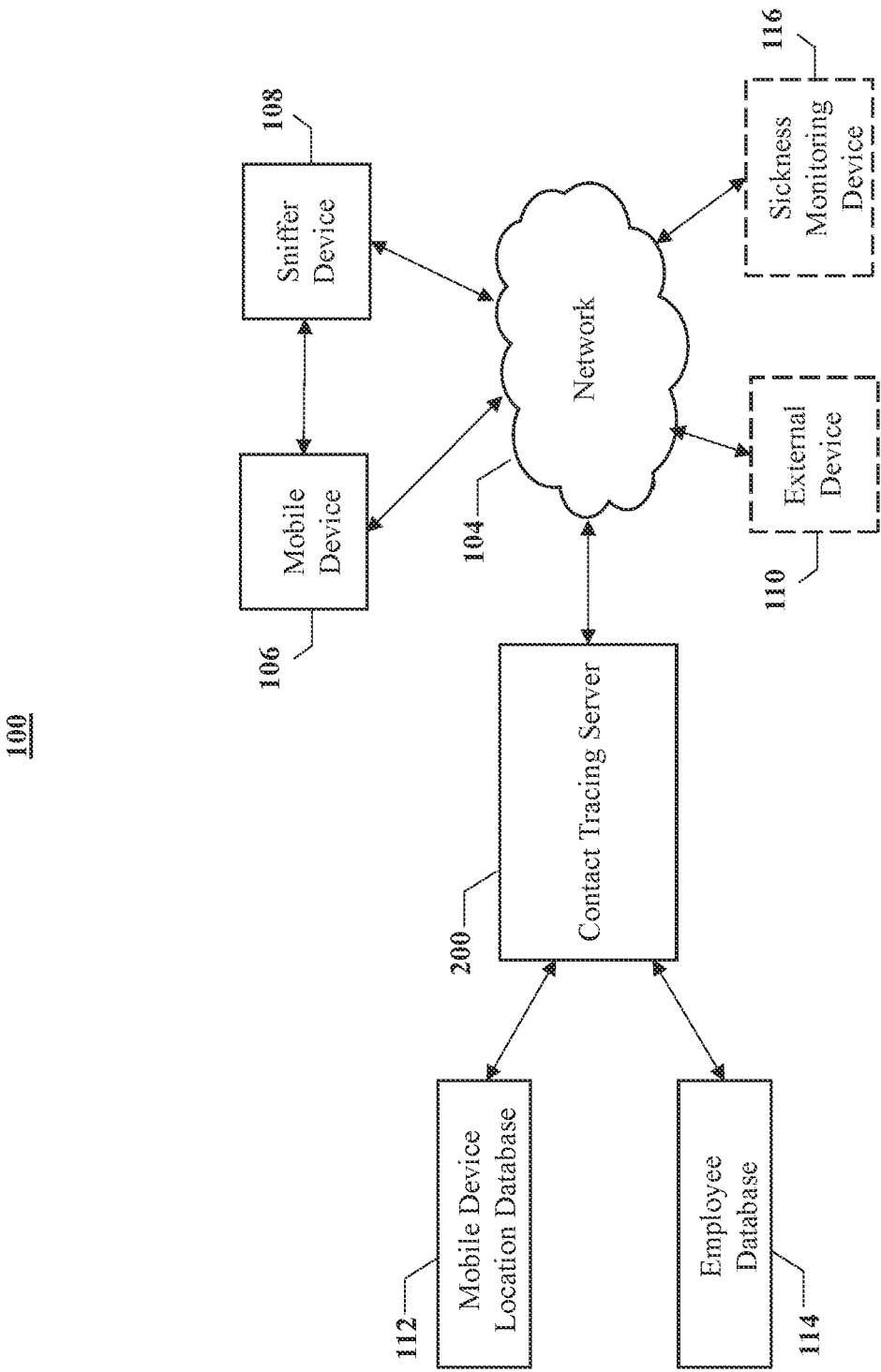
FIG. 1 illustrates a system diagram including devices that may be involved in some example embodiments described herein.

Some embodiments of the present disclosure will now be described more fully hereinafter with reference to the accompanying drawings, in which some, but not all embodiments are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout. As used herein, the description may refer to a responsive contact tracing server as an example "apparatus." However, elements of the apparatus described herein may be equally applicable to the claimed method and computer program product. Thus, use of any such terms should not be taken to limit the spirit and scope of embodiments of the present disclosure.

Overview

Contact tracing is a relatively well-established method used by various entities to track down the source of a disease and take proactive measures to control its spread. Traditionally, this may be done through questionnaires. Upon diagnosis of a disease, the infected person may be asked to list all the places they've visited and the individuals they've interacted with. This patient information can then be used to contact possibly affected individuals, places, etc. However, depending on the disease type, there is an incubation period, typically between 2-14 days, from the time of infection and the onset of symptoms. It can be difficult for infected individuals to recollect where they've been over the course of their illness and is therefore error prone.

One approach to overcome these difficulties is to use a contact tracing app. When a contact tracing app is installed, Bluetooth capable devices, such as smartphones, may detect other Bluetooth capable devices within a certain proximity from the device. This allows the mobile device to keep a log of any devices by recording a device ID associated with the mobile device, the associated time of contact, and in some cases, the proximity range. When an individual is diagnosed with a disease, their device ID is used by other mobile devices to determine if they have been within the proximity of the other individuals. However, the problem with this method is that it requires individuals to have downloaded and installed the app on the mobile device that they routinely carry with them. Otherwise, the movements and position of the individual will not be recorded. Therefore, this client-side approach is ineffective unless a significant portion of individuals in a given region utilize the app.

Another approach is the use of a network-centric contact tracing system. This may be done using a system of sniffer devices, such as Wi-Fi access points, that may localize an individual's mobile device. A network associated with the sniffer devices may detect all mobile devices connected to it at all times, without requiring an individual to download an app or opt-in to any program. In a workplace setting, such as an office building, sniffer devices, such as these Wi-Fi access points, are typically already in place, though not conventionally used for such a process. However, it can be difficult to link a mobile device to a particular individual without direct input from said individual.

Embodiments of the present disclosure are provided to address the problems arising out of the deficient technical nature of conventional systems. Indeed, embodiments of the present disclosure provide various technical improvements in the technical field of contact tracing. In this regard, embodiments of the present provide more accurate methods for contact tracing by leveraging existing technology in the workplace and utilize this technology in unconventional ways. For example, existing Wi-Fi access points in an office may be leveraged to track all mobile devices broadcasting a wireless signal and provide that information to a central server or store the information to a network database. This does not require the individual to download any app or perform any extraneous task. When an employee enters the range of the sniffer network, e.g. enters the workplace, one or more of their mobile devices may be detected and tracked by the sniffer network throughout their workday. Additionally or alternatively, embodiments of the present disclosure further provide improvement by associating an employee with one or more of their mobile devices. For example, an employee database may store various employee parameters such as badge ID number and biometric data. When there is an indication of an employee's identity, such as when they clock in with an external device, such as a badge, the identified employee may be associated with one or more mobile devices within the same vicinity as said employee. The device ID of the one or more mobile devices may be stored as an additional parameter in the employee database. Additionally or alternatively, embodiments of the present disclosure further provide improvements by allowing for automatic sickness detection such that the infected employee may be identified and the disease may proactively be stopped from spreading. For example, thermometer monitors, such as IR detectors, may detect an abnormal body temperature from an employee and in response, send a notification that the employee is sick. In another example, a network of microphones may monitor the workplace for auditory symptoms of sickness, such as coughing, sneezing, and/or sniffling, and send a notification that the employee is sick.

Definition of Terms

As used herein, the terms "data," "content," "information," "electronic information," "signal," "command," and similar terms may be used interchangeably to refer to data capable of being transmitted, received, and/or stored in accordance with embodiments of the present disclosure. Thus, use of any such terms should not be taken to limit the spirit or scope of embodiments of the present disclosure. Further, where a first computing device is described herein to receive data from a second computing device, it will be appreciated that the data may be received directly from the second computing device or may be received indirectly via one or more intermediary computing devices, such as, for example, one or more servers, relays, routers, network access points, base stations, hosts, and/or the like, sometimes referred to herein as a "network." Similarly, where a first computing device is described herein as sending data to a second computing device, it will be appreciated that the data may be sent directly to the second computing device or may be sent indirectly via one or more intermediary computing devices, such as, for example, one or more servers, remote servers, cloud-based servers (e.g., cloud utilities), relays, routers, network access points, base stations, hosts, and/or the like.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

As used herein, the phrases "in one embodiment," "according to one embodiment," "in some embodiments," and the like generally refer to the fact that the particular feature, structure, or characteristic following the phrase may be included in at least one embodiment of the present disclosure. Thus, the particular feature, structure, or characteristic may be included in more than one embodiment of the present disclosure such that these phrases do not necessarily refer to the same embodiment.

As used herein, the word "example" is used herein to mean "serving as an example, instance, or illustration." Any implementation described herein as "example" is not necessarily to be construed as preferred or advantageous over other implementations.

As used herein, the terms "mobile device,", "first mobile device", "second mobile device", and the like refer to computer hardware and/or software that is configured to access a service made available by the responsive contact tracing server and, among various other functions, is configured to directly, or indirectly, transmit and receive at least device data. Example mobile devices may include a smartphone, a tablet computer, a laptop computer, a wearable device (e.g., smart glasses, smartwatch, badge with RFID or the like), and the like. In some embodiments, a mobile device may include a "smart device" that is equipped with chip of other electronic device that is configured to communicate with the responsive contact tracing server via Bluetooth, NFC, Wi-Fi, 3G, 4G, 5G, RFID protocols, and the like. By way of a particular example, a mobile device may be a smartphone and a second mobile device may be a laptop, where each mobile device is equipped with a Wi-Fi radio that is configured to communicate with a Wi-Fi access point that is in communication with the server (e.g., a responsive contact tracing server of the present disclosure) via a network.

As used herein, the term "sniffer device", "sniffer device grid", "system of sniffer devices" and the like refers to hardware and/or associated software capable of passively monitoring internet traffic in real time. By way of example, Wi-Fi access points (APs) may detect Wi-Fi signals from any mobile device within a designated area such that the device is "sniffed". As the mobile device moves through a workplace, its wireless signal may be picked up by other Wi-Fi APs such that the location of the mobile device throughout a workplace is known.

As used herein, the term "employee database" and "mobile device location database" refer to data structures or repositories for storing profiles and associated parameters. In the case of the employee database, employee profile parameters of the may refer to data stored in a user profile for the particular user. By way of example, the employee profile parameters may include user data regarding the name, occupation, office location, badge ID number, biometric data, associated mobile devices, etc. of the respective employees. Furthermore, the employee profile parameters may be updated dynamically to reflect the most up-to-date information associated with an employee. By way of example, the employee profile parameters of a first employee profile not currently associated with a mobile device may be updated such that one or more mobile devices are associated with said first employee. Similarly in the case of the mobile device location database, mobile device profile parameters may refer to data stored in a mobile device profile for the particular mobile device. By way of example, the mobile device location parameters may include a mobile device ID, location of a sniffer device that detected the mobile device's wireless signal, and the detection time at which the signal was detected. These parameters may be dynamically and continuously updated such that the mobile device location database has the most up-to-date information for a mobile device in the associated mobile device's profile.

The term "mobile device identification data", "first mobile device identification data", "device identification data", or "identification data" as used herein refers to any information that may identify a computing device, such as a mobile phone or laptop. For example, device identification information may refer to a user's subscriberID, which may be similar or the same as a mobile device's phone number/CallerID number, the mobile device's phone number, the mobile device's callerID number, International Mobile Equipment Identity (IMEI)/unique serial number (ICCID) data, network-based, MAC addresses, billing record's modem certificate, DOCSIS hub/Media Access Layer routing assignments, Cable modem's certificate, device serial number, etc., Intel vPro and Trusted Platform Module key, or the like. In a mobile context, device identification information may refer to a subscriber identification module (SIM), embodied by SIM cards, which are configured to store network-specific information used to authenticate and identify subscribers on a network, and may further be embodied by e-sims, programmable sims, virtual sims, apple sims, or the like, Universal Subscriber Identity Module (USIM), a Removable User Identity Module (R-UIM), or a CDMA Subscriber Identity Module (CSIM), any of which may be a software application or integrated circuit, for example, stored on a SIM card or Universal Integrated Circuit Card (UICC), may comprise at least a unique serial number (ICCID), an international mobile subscriber identity (IMSI) number, Authentication Key (Ki), Local Area Identity (LAI), and Operator-Specific Emergency Number. SIM cards also store other carrier specific information such as, for example, the SMSC (Short Message Service Center) number, Service Provider Name (SPN), Service Dialing Numbers (SDN), Advice-Of-Charge parameters, and Value Added Service (VAS) application. The SIM card, as referred to herein, may be a full, mini, micro, nano, virtual, programmable, software (e.g., "soft" sim), an Apple®, or an emdedded(e) SIM. In some embodiments, device identification information may be contained within, stored on, or otherwise embodied by an EMV (Europay, MasterCard and Visa) chip or an NFC (Near Field Communication) chip with, for example, unique account information. Device identification information may be stored, transmitted, and/or received, in some embodiments, in a raw, tokenized, hashed, one-way hashed, encrypted, digitally signed, using public/private key encryption or other means of encrypting, or other similar algorithms (e.g., for system/customer/bank/wireless network/other privacy or other reasons) data form, or otherwise derived or transcoded from any of the above.

As used herein, the term "computer-readable medium" refers to non-transitory storage hardware, non-transitory storage device or non-transitory computer system memory that may be accessed by a controller, a microcontroller, a computational system or a module of a computational system to encode thereon computer-executable instructions or software programs. A non-transitory "computer-readable medium" may be accessed by a computational system or a module of a computational system to retrieve and/or execute the computer-executable instructions or software programs encoded on the medium. Exemplary non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM), and the like.

Device Architecture and Example Apparatus

Having set forth a series of definitions called-upon throughout this application, an example system architecture and example apparatus is described below for implementing example embodiments and features of the present disclosure.

With reference to FIG. 1, an example system 100 is illustrated with an apparatus (e.g., a contact tracing server 200) communicably connected via a network 104 to a mobile device 106, a sniffer device 108, and, in some embodiments, an external device 110 and/or a sickness monitoring device 116. The example system 100 may also include a mobile device location database 112 and employee database 114 that may be hosted by the contact tracing server 200 or otherwise hosted by devices in communication with the contact tracing server 200.

The contact tracing server 200 may include circuitry, networked processors, or the like configured to perform some or all of the apparatus-based (e.g., contact tracing server-based) processes described herein, and may be any suitable network server and/or other type of processing device. In this regard, mobile device 106 may be embodied by any of a variety of devices. For example, the contact tracing server 200 may be configured to receive input data (e.g., mobile device location data) and may include any of a variety of fixed terminals, such as a server, desktop, or kiosk, or it may comprise any of a variety of mobile terminals, such as a portable digital assistant (PDA), mobile telephone, smartphone, laptop computer, tablet computer, or in some embodiments, a peripheral device that connects to one or more fixed or mobile terminals. Example embodiments contemplated herein may have various form factors and designs, but will nevertheless include at least the components illustrated in FIG. 2 and described in connection therewith. In some embodiments, the contact tracing server 200 may be located remotely from the mobile device 106, sniffer device 108, external device 110, sickness monitoring device 116, mobile device location database 112, and/or employee database 114, although in other embodiments, the contact tracing server 200 may comprise the mobile device 106, sniffer device 108, external device 110, sickness monitoring device 116, mobile device location database 112, and/or employee database 114. The contact tracing server 200 may, in some embodiments, comprise several servers or computing devices performing interconnected and/or distributed functions. Despite the many arrangements contemplated herein, the contact tracing server 200 is shown and described herein as a single computing device to avoid unnecessarily overcomplicating the disclosure.

The network 104 may include one or more wired and/or wireless communication networks including, for example, a wired or wireless local area network (LAN), personal area network (PAN), metropolitan area network (MAN), wide area network (WAN), or the like, as well as any hardware, software and/or firmware for implementing the one or more networks (e.g., network routers, switches, hubs, etc.). For example, the network 104 may include a cellular telephone, mobile broadband, long term evolution (LTE), GSM/EDGE, UMTS/HSPA, IEEE 802.11, IEEE 802.16, IEEE 802.20, Wi-Fi, dial-up, and/or WiMAX network. Furthermore, the network 104 may include a public network, such as the Internet, a private network, such as an intranet, or combinations thereof, and may utilize a variety of networking protocols now available or later developed including, but not limited to TCP/IP based networking protocols.

The mobile device 106 may be associated with a first employee and first employee profile. Although a single mobile device associated with a corresponding employee profile is shown, the example system 100 may include any number of mobile devices that may be associated with various employee and/or employee profiles. The mobile device 106 may be a cellular telephones (e.g., a smartphone and/or other type of mobile telephone), laptop, tablet, electronic reader, e-book device, media device, wearable, smart glasses, smartwatch, or any combination of the above.

The sniffer device 108 may include an apparatus capable of detecting wireless signals from any number of mobile devices. The sniffer device 108 may be a wireless access point, Bluetooth access point, or any apparatus capable of detecting a wireless signal from a mobile device. Although a single sniffer device is shown, the example system 100 may include any number of sniffer devices that. The combination of associated sniffer devices 108 define a sniffer grid.

The external device 110, as defined above, may be associated with any entity that is not associated with the mobile device 106, sniffer device 108, or sickness detection device 116. By way of a more particular example, the external device 110 may include a server of a workplace or other $3^{rd}$ party configured to be in secure communication with the mobile device 106 and/or sniffer device 108 via the network 104. Although shown as a single external device 110, the system 100 may include any number of external devices.

The sickness monitoring device 116 may include an apparatus capable of recording and monitoring all employees in a specific area. In some embodiments the sickness monitoring device 116 may be an IR sensor capable of measuring an employee's temperature. In some embodiments, the sickness monitoring device 116 may include one or more microphones to monitor auditory surroundings. Although shown as a single sickness monitoring device 116, the system 100 may include any number of sickness monitoring devices. The combination of associated sickness monitoring devices 116 define a sickness monitoring grid.

The mobile device location database 112 may be any suitable storage device configured to store some or all of the information described herein (e.g., memory 204 of the contact tracing server 200 or a separate memory system separate from the contact tracing server 200, such as one or more database systems, backend data servers, network databases, cloud storage devices, or the like provided by an external device 110 (e.g., a workplace entity or 3r d party provider) or the mobile device 106). The mobile device location database 112 may include data received from the contact tracing server 200 (e.g., via a memory 204 and/or processor(s) 202) and/or the sniffer device 108, and the corresponding storage device may thus store this data. This data may include a mobile device ID, time of detection, and sniffer device identification data. Sniffer device identification data may include an assigned sniffer device ID, building identity, room number, room purpose, or other location data.

The employee database 114 may be any suitable storage device configured to store some or all of the information described herein (e.g., memory 204 of the contact tracing server 200 or a separate memory system separate from the contact tracing server 200, such as one or more database systems, backend data servers, network databases, cloud storage devices, or the like provided by an external device 110 (e.g., a workplace entity or 3r d party provider) or the mobile device 106). The employee database 114 may include data received from contact tracing server 200 (e.g., via a memory 204 and/or processor(s) 202), and the corresponding storage device may thus store this data. This data may include an employee's associated mobile device IDs. The employee database may also have parameters corresponding to an employee's name, occupation, office location, badge ID number, biometric data, or the like.

It will be noted, however, that the employee database 114 may be a distinct storage device from the device mobile device location database 112 storage device or may be stored by the same storage device. To avoid unnecessarily overcomplicating the disclosure, the mobile device location database 112 and employee database 114 are shown and described using corresponding blocks, despite the fact that they may each be hosted by any number of specific physical devices, together or separately.

Figure 2:
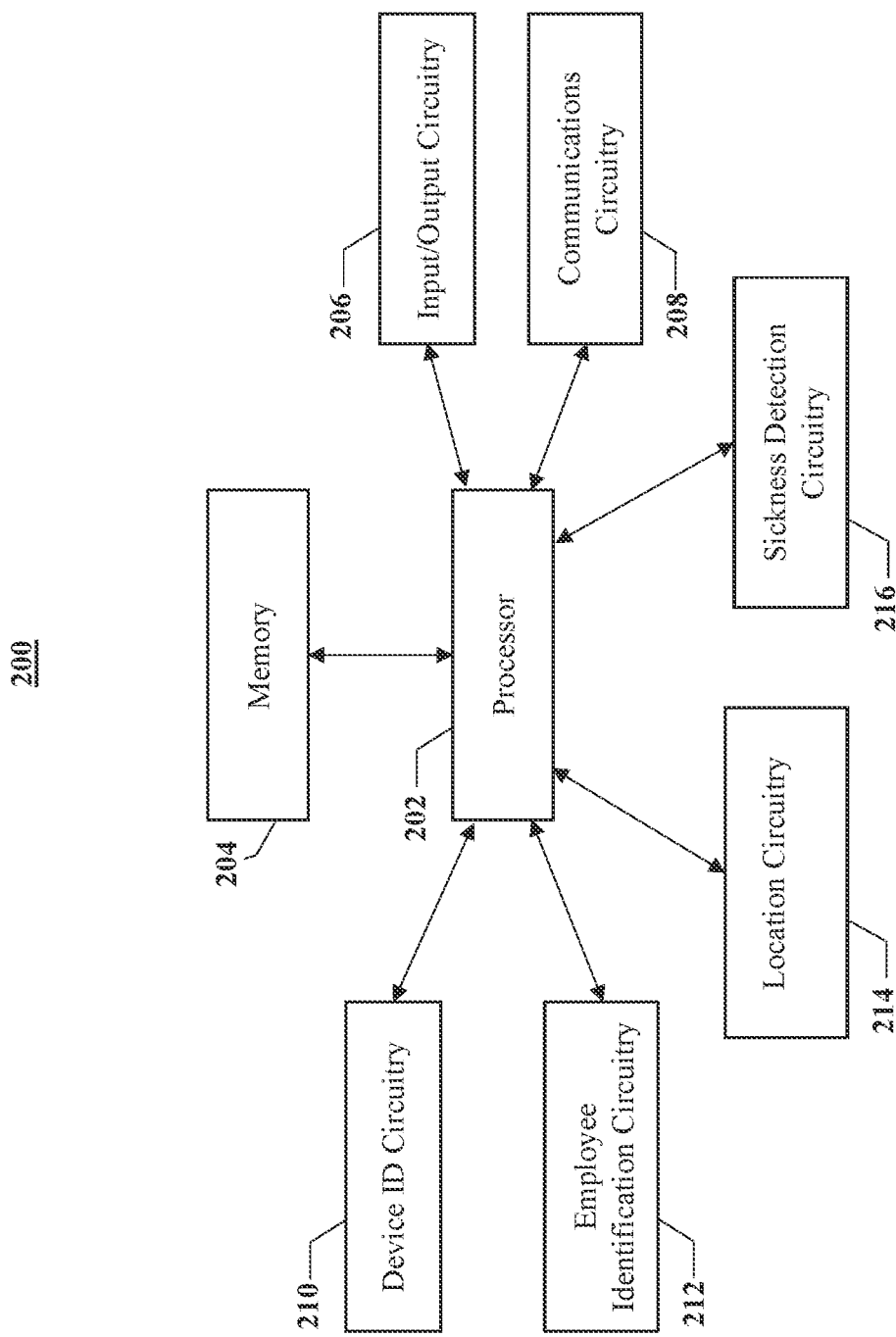
FIG. 2 illustrates a schematic block diagram of example circuitry that may perform various operations, in accordance with some example embodiments described herein.

As illustrated in FIG. 2, the contact tracing server 200 may include a processor 202, a memory 204, input/output circuitry 206, and communications circuitry 208. Moreover, contact tracing server 200 may include device ID circuitry 210, employee identification circuitry 212, location circuitry 214, and sickness detection circuitry 216. The contact tracing server 200 may be configured to execute the operations described below in connection with FIGS. 3-5. Although components 202-216 are described in some cases using functional language, it should be understood that the particular implementations necessarily include the use of particular hardware. It should also be understood that certain of these components 202-216 may include similar or common hardware. For example, two sets of circuitry may both leverage use of the same processor 202, memory 204, communications circuitry 208, or the like to perform their associated functions, such that duplicate hardware is not required for each set of circuitry. The use of the term "circuitry" as used herein includes particular hardware configured to perform the functions associated with respective circuitry described herein. As described in the example above, in some embodiments, various elements or components of the circuitry of the contact tracing server 200 may be housed within one or more of the mobile devices 106 or an external device 110. As indicated previously, it will be understood in this regard that some of the components described in connection with the contact tracing server 200 may be housed within one of these devices, while other components are housed within another of these devices, or by yet another device not expressly illustrated in FIG. 1.

Of course, while the term "circuitry" should be understood broadly to include hardware, in some embodiments, the term "circuitry" may also include software for configuring the hardware. For example, although "circuitry" may include processing circuitry, storage media, network interfaces, input/output devices, and the like, other elements of the contact tracing server 200 may provide or supplement the functionality of particular circuitry.

In some embodiments, the processor 202 (and/or co-processor or any other processing circuitry assisting or otherwise associated with the processor) may be in communication with the memory 204 via a bus for passing information among components of the contact tracing server. The memory 204 may be non-transitory and may include, for example, one or more volatile and/or non-volatile memories. In other words, for example, the memory may be an electronic storage device (e.g., a non-transitory computer readable storage medium). The memory 204 may be configured to store information, data, content, applications, instructions, or the like, for enabling the contact tracing server to carry out various functions in accordance with example embodiments of the present invention.

The processor 202 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the contact tracing server, and/or remote or "cloud" processors.

In an example embodiment, the processor 202 may be configured to execute instructions stored in the memory 204 or otherwise accessible to the processor 202. Additionally or alternatively, the processor 202 may be configured to execute hard-coded functionality. As such, whether configured by hardware or by a combination of hardware with software, the processor 202 may represent an entity (e.g., physically embodied in circuitry) capable of performing operations according to an embodiment of the present invention while configured accordingly. In an exemplary embodiment, when the processor 202 is embodied as an executor of software instructions, the instructions may specifically configure the processor 202 to perform the algorithms and/or operations described herein when the instructions are executed.

The contact tracing server 200 further includes input/output circuitry 206 that may, in turn, be in communication with processor 202 to provide output to a user and to receive input from a user, user device, or another source (e.g., so as receive mobile device location data or employee identification data). In this regard, the input/output circuitry 206 may comprise a display that may be manipulated by a mobile application. In some embodiments, the input/output circuitry 206 may also include additional functionality keyboard, a mouse, a joystick, a touch screen, touch areas, soft keys, a microphone, a speaker, or other input/output mechanisms. The processor 202 and/or user interface circuitry comprising the processor 202 may be configured to control one or more functions of a display through computer program instructions (e.g., software and/or firmware) stored on a memory accessible to the processor (e.g., memory 204, and/or the like), so as receive mobile device location data or employee data.

The communications circuitry 208 may be any means such as a device or circuitry embodied in either hardware or a combination of hardware and software that is configured to receive and/or transmit data from/to a network and/or any other device, circuitry, or module in communication with the contact tracing server 200. In this regard, the communications circuitry 208 may include, for example, a network interface for enabling communications with a wired or wireless communication network. For example, the communications circuitry 208 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s). These signals may be transmitted by the contact tracing server 200 using any of a number of wireless personal area network (PAN) technologies, such as Bluetooth® v1.0 through v3.0, Bluetooth Low Energy (BLE), infrared wireless (e.g., IrDA), ultra-wideband (UWB), induction wireless transmission, or the like. In addition, it should be understood that these signals may be transmitted using Wi-Fi, Near Field Communications (NFC), Worldwide Interoperability for Microwave Access (WiMAX) or other proximity-based communications protocols.

Device ID circuitry 210 includes hardware components designed to generate a unique device ID for any mobile device 106 detected by a sniffer device 108. These hardware components may, for instance, utilize elements of processor 202 or memory 204 to identify a mobile device 106 based on its wireless signal. If it is determined, by way of processor 202 and memory 204 that the mobile device 106 does not have a corresponding device ID, then a device ID may be generated by way of the processor 202 and the information stored in memory 204 and/or mobile device location database 112. The generated device ID may contain integers, letters, or a combination of integers and letter such that no device ID corresponding to one mobile device is the same as a device ID corresponding to a different mobile device. In some embodiments, the device ID may utilize decimal, binary, octal, or hexadecimal numbering schemes.

Employee identification circuitry 212 includes hardware components designed to identify an employee based on employee identification data. These hardware components may, for instance, utilize elements of processor 202 or memory 204 to identify an indication of employee identification data. In some embodiments, employee identification circuitry 212 may be communicatively coupled to input/output circuitry 206 and/or communications circuitry 208 to receive employee identification data from an external device 110. Employee identification data may contain values for one or more employee parameters as found in the employee database. In some embodiments, upon receiving an indication of employee identity, employee identification circuitry 212 may access the employee database 114 to identify the employee whose employee profile is associated with the one or more parameters as supplied by the employee identification data.

Location circuitry 214 includes hardware components designed to determine the location of a mobile device 106. These hardware components may, for instance, utilize elements of processor 202 or memory 204 to determine the location of one or more mobile devices. In some embodiments, the location circuitry 214 may be communicatively coupled to input/output circuitry 206 to receive at least a mobile device ID, a proximate distance, and a time period. The proximate distance and time period may be configured by a user using input/output circuitry 206. Location circuitry 214 may access the mobile device location database 112 to view mobile device location data entries associated with a particular mobile device ID. The mobile device location data entries may include at least a mobile device ID, identification data of the sniffer device which detected the mobile device, and a corresponding detection time. The location circuitry 214 may then utilize the processor 202 to determine the location of the mobile device 106 over the specified period. The location circuitry 214 may also generate a list of every mobile device ID that came within the proximate distance of the target mobile device ID over the specified period of time.

In some embodiments, the location circuitry 214 may receive an employee identifier instead of or in addition to a mobile device ID. Prior to accessing the mobile device location database 112, the location circuitry may first access the employee database 114 based on the received employee identifier, identify a corresponding employee profile in the employee database 114, and determine any associated mobile device IDs. The location circuitry 214 may then access the mobile device location database 112 using the associated mobile device IDs and perform the aforementioned operations and generate a list of every mobile device ID that came within the proximate distance of the employee over the specified period of time.

Sickness detection circuitry 214 includes hardware components designed to detect if an employee is exhibiting symptoms of an illness. In some embodiments, sickness detection circuitry 214 may be configured to detect signs of illness based on input received from sickness monitoring device 116. For example, sickness monitoring device 116 may record an employee's temperature throughout the day. Sickness detection circuitry 214 may be configured to accept a configurable temperature range. In the event an employee's temperature is above or below the acceptable range, the sickness detection circuitry 214 may generate an alert by means of the processor 202. In some embodiments, the sickness detection circuitry 214 is communicatively coupled to input/output circuitry 206 and/or communications circuitry 208 such that the alert may be sent to one or more configured mobile devices.

It should also be appreciated that, in some embodiments, the device ID circuitry 210, employee identification circuitry 212, location circuitry 214, or sickness detection circuitry 216 may include a separate processor, specially configured field programmable gate array (FPGA), or application specific interface circuit (ASIC) to perform its corresponding functions.

In addition, computer program instructions and/or other type of code may be loaded onto a computer, processor or other programmable contact tracing server's circuitry to produce a machine, such that the computer, processor other programmable circuitry that execute the code on the machine create the means for implementing the various functions, including those described in connection with the components of contact tracing server 200.

As described above and as will be appreciated based on this disclosure, embodiments of the present invention may be configured as systems, methods, mobile devices, and the like. Accordingly, embodiments may comprise various means including entirely of hardware or any combination of software with hardware. Furthermore, embodiments may take the form of a computer program product comprising instructions stored on at least one non-transitory computer-readable storage medium (e.g., computer software stored on a hardware device). Any suitable computer-readable storage medium may be utilized including non-transitory hard disks, CD-ROMs, flash memory, optical storage devices, or magnetic storage devices.

Example Operations for Passive Contact Tracing

Figure 3:
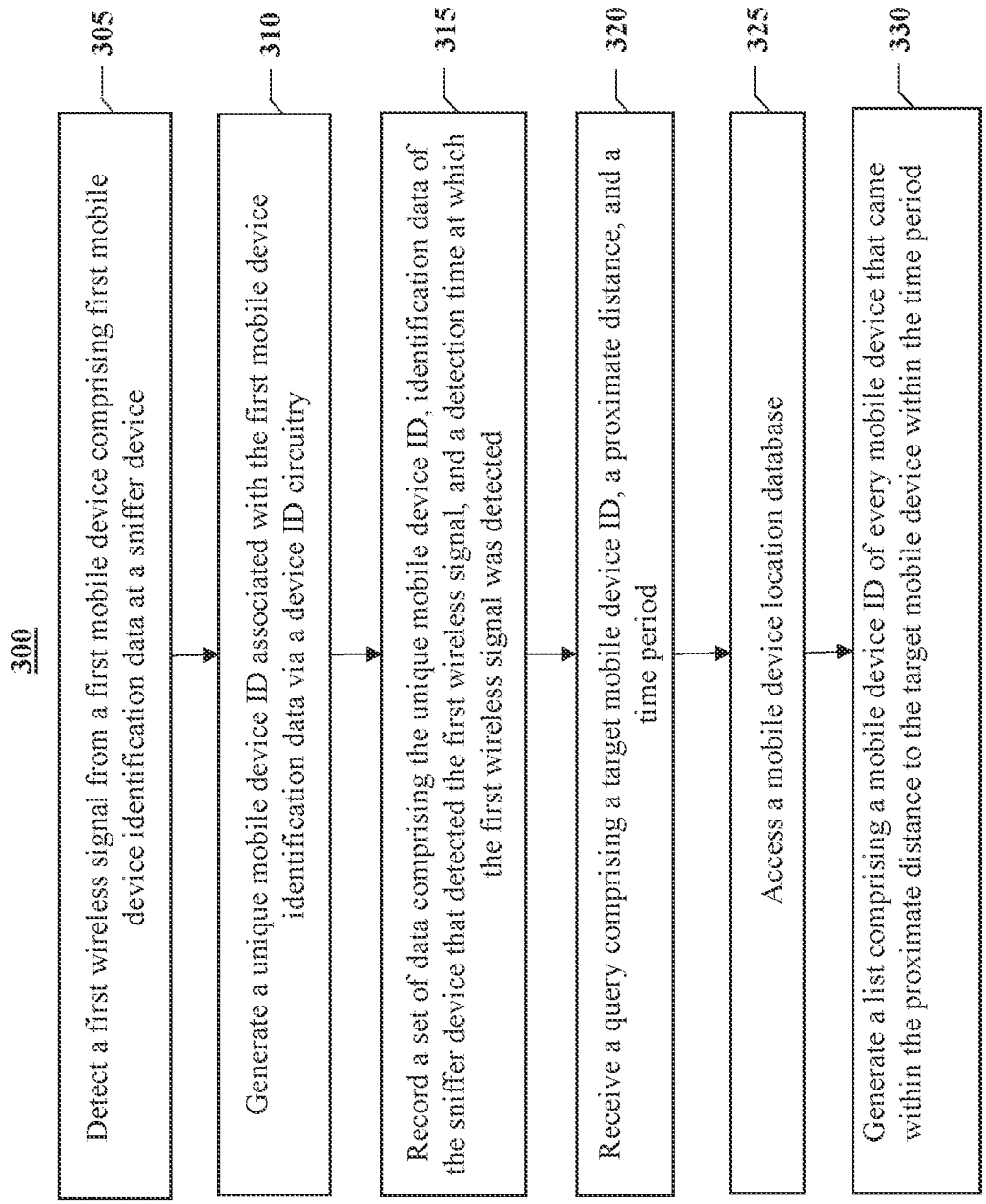
FIG. 3 illustrates an example flowchart for passively tracking sick employees, in accordance with some example embodiments described herein.

FIG. 3 illustrates a flowchart 300 containing a series of operations for passive contact tracing. The operations illustrated in FIG. 3 may, for example, be performed by, with the assistance of, and/or under the control of an apparatus (e.g., contact tracing server 200), as described above. In this regard, performance of the operations may invoke one or more of processor 202, memory 204, input/output circuitry 206, communications circuitry 208, device ID circuitry 210, employee identification circuitry 212, location circuitry 214, and/or sickness detection circuitry 216.

As shown in operation 305, a sniffer device 108 detects a first wireless signal from a first mobile device 106 comprising first mobile device identification data. In some embodiments, contact tracing server 200, device ID circuitry 210 or the like may be configured to receive, from the sniffer device 108, information indicative of a detection of the first wireless signal from the first mobile device 106. In some example embodiments, as described above and below with reference to FIG. 5, the sniffer device 108 may detect wireless signals from each of a plurality of mobile devices 106. By way of example, the sniffer device 108 may be a Wi-Fi access point that projects a Wi-Fi signal within an encompassed range. This is shown later in more detail with respect to FIGS. 6 and 7. When a mobile device 106 with Wi-Fi capabilities enters this encompassed range, the mobile device 106 may emit a wireless signal detectable by the sniffer device 108. The wireless signal emitted by the first mobile device 106 may contain first mobile device identification data.

The sniffer device 108 that detected the wireless signal from the first mobile device 106 may be associated with identification data. This identification data may include a sniffer device ID, building identity, room number, room purpose, or other location data. Additionally or alternatively, memory 204 may store associated information for a particular sniffer device ID such as location of the sniffer device relative to other sniffer devices, an associated encompassed range of the sniffer device, and/or a physical location in a building. As a non-limiting example, a sniffer device may have a device ID that indicates it is positioned in the entry-way of a building at 123 Main St., New York NY 10030 and has an encompassed range up to 100 feet away.

Thereafter, as shown in operation 310, the apparatus (e.g., contact tracing server 200) includes means, such as device ID circuitry 210 or the like, for generating a unique mobile device ID associated with the first mobile identification data. In some embodiments, the device ID circuitry 210 may access memory 204 to determine if the mobile device identification data already has been assigned a unique mobile device ID and if so, will return the unique mobile device ID corresponding to the mobile device identification data. Otherwise, the device ID circuitry 210 will generate a unique mobile device ID.

Thereafter, as shown in operation 315, the apparatus (e.g. contact tracing server 200) may include means, such as processor 202, memory 204, communications circuitry 208, device ID circuitry 210, or the like, for recording, storing to memory, or the like, a set of data that may include, for example, one or more of mobile device identification information, such as the unique mobile device ID returned or generated in operation 310, identification data of the sniffer device 108 that detected the first wireless signal, and a detection time at which the wireless signal was detected. In some embodiments, the set of data may be stored in the mobile device location database 112.

In some embodiments, the set of data may be recorded to the mobile location database 112 continuously as long as the mobile device 106 is within the encompassed range of sniffer device 108. In some embodiments, the set of data may be recorded to the mobile location database 112 periodically over an interval of time. For example, the set of data may be recorded every second, every 5 seconds, or the like. In some embodiments, only the start time at which the mobile device 106 is detected and the end time at which the mobile device 106 is no longer detectable by the sniffer device 108 is recorded. In all embodiments, a duration of time the mobile device 106 remains within the encompassed range of sniffer device 108 is determinable.

Thereafter, as shown in operation 320, the apparatus (e.g. contact tracing server 200) may include means, such as processor 202, communications circuitry 208, location circuitry 214, or the like, for receiving a query that includes a target mobile device ID or any information that may be associated with or linked to first mobile identification data and/or the unique mobile device ID described above, a proximate distance, and a time period. In some embodiments, in order to generate a query, a user may have to enter credentials to authorize such a query. As such, private information is kept secure and only accessed by authorized personal. Similarly, if a manual review of the information stored in the mobile device location database 112 and/or employee database 114 is desired, a user may be required to enter credentials to gain access into the database.

In some embodiments, the query may contain an employee identifier, for example, that may be linked to or associated with a target mobile device ID instead of or in addition to a target mobile device ID. The location circuitry 214 may, by way of processor 202, access the employee database 114. Using the provided employee identifier, the location circuitry 214 may access the employee profile associated with the employee identifier and identify at least one mobile device ID associated with the employee. In some embodiments, all mobile device IDs associated with the employee are identified. The location circuitry 214 may then, by way of processor 202, generate a new query or modify the original query to include the one or more mobile device IDs identified as associated with the employee from the employee database 114 as well as the proximate distance, and time period from the original query.

In some embodiments, the query may include identification information and a disease name or moniker. The location circuitry 214, by means of processor 202, memory 204, input/output circuitry 206, and/or communications circuitry 208 may obtain relevant epidemiological data for the disease in the query, such as recommended proximate distance and infectivity time period, which may serve as proxies for the proximate distance and the time period in a subsequent query. In some embodiments a local database may store this information. In some embodiments, communications circuitry 208 may access a government or health database for this information. Upon obtaining this information, location circuitry 214 will create a new query or modify the original query to include at least the determined proximate distance and/or infectivity time period.

As a non-limiting example, a query may be received by location circuitry 214 that includes an employee name "Jane Doe" and a disease moniker "Covid-19". The location circuitry 214 may first obtain the device IDs associated with employee Jane Doe from the employee database 114 or obtain epidemiological data for Covid-19 from a local database. Alternatively, location circuitry 214 may simultaneously execute these operations. The location circuitry 214 may determine Jane Doe has one associated mobile device and Covid-19 has an associated proximate distance of six feet and a time period of 14 days. Location circuitry 214 may then generate a new query using the device ID associated with Jane Doe and the proximate distance and time period values associated with Covid-19 of six feet and 14 days.

Thereafter, as shown in operation 325, the apparatus (e.g. contact tracing server 200) may include means, such as processor 202, communications circuitry 208, location circuitry 214, or the like, for accessing a mobile device location database 112. As described above with respect to operation 320, a query that includes at least a device ID, a proximate distance, and a time period is received by the location circuitry 214. Location circuitry 214 may then, by means of communications circuitry 208 and/or processor 202, access the mobile device database 112. Based on the mobile device ID from the query, the location of the mobile device over time may be found. The time for which the mobile device is listed is restricted to the time period received from the query. In some embodiments, a time period may include a time range and/or a day of interest. As a non-limiting example, an infected employee who last reported to work on Friday, Aug. 28, 2020, may have been diagnosed with an illness that has an infectious period of 14 days. The infectious period may occur before, during, or after the onset of symptoms. The location circuitry 214 may pull all location data associated with the employee's one or more mobile device IDs from Friday, Aug. 14, 2020 to Friday, Aug. 28, 2020, i.e. 14 days.

Thereafter, as shown in operation 330, the apparatus (e.g. contact tracing server 200 may include means, such as processor 202, memory 204, input/output circuitry 206, communications circuitry 208, location circuitry 214, or the like, for accessing memory and generating a list that includes a mobile device ID of every mobile device that came within the proximate distance to the target mobile device within the specified time period. In operation 325, the location data associated with a target mobile device ID is restricted to a certain time frame. Within this time frame, location circuitry 214 may utilize the proximate distance parameter to generate a list of all other mobile device that came within the proximate distance of the target mobile device ID. That is, the apparatus (e.g. contact tracing server 200 may include means, such as processor 202, memory 204, input/output circuitry 206, communications circuitry 208, location circuitry 214, or the like, for accessing a database in which information detailing location information of particular devices at particular times is stored, and determining those instances in which a second mobile device is co-located with the target mobile device (e.g., has location information identifying a particular location the same as or within a threshold distance to that of the target mobile device at the same time or within a specified time period—e.g., both in the breakroom at 9:05 am on certain date, or the like). As will be described in further detail for FIGS. 6 and 7, the proximate distance from a target mobile device to a different mobile device may be triangulated using co-detections from two or more sniffer devices. The sensitivity of a sniffer network may be refined by adding sniffer devices. Location circuitry 214 may generate the list of all devices determined to have come with said proximate distance from the target mobile device. In some embodiments, the number of times a particular mobile device ID has been exposed to the target mobile device ID over the period of time as well as total duration of time of estimated exposure may also be included in the list.

In some embodiments, the location circuitry 214 may access the employee database 112, by means of communications circuitry 208, and further generate a list comprising one or more employee identifiers, for example, each being associated with at least one mobile device from the list. In some embodiments, if the same employee is found to be associated with two or more devices, location circuitry 214 may consolidate the data entry to include one instance of the employee identifier and list the associated mobile devices together. In this way, extraneous data entries are eliminated.

In some embodiments, the list is output, by means such as processor 202, input/output circuitry 206, and/or communications circuitry 208, for example, to the authorized user who generated the query. That is, the apparatus (e.g. contact tracing server 200) may include means, such as processor 202, memory 204, input/output circuitry 206, communications circuitry 208, location circuitry 214, or the like, for outputting the list, e.g., via a display, printer, or the like. The authorized user may review the list and decide whether further action is needed. In some embodiments, the apparatus (e.g. contact tracing server 200) may include means, such as processor 202, memory 204, input/output circuitry 206, communications circuitry 208, location circuitry 214, or the like, for automatically performing further action. For example, further action may include generating and/or transmitting an email, SMS message, or the like to the employees determined to have been exposed to the disease. In some embodiments, further action may include closing down areas where the infected employee was determined to have visited during the time period for sanitation purposes.

In some embodiments, an indication that an employee is sick may be determined at the workplace. This may advantageously prevent the spread of disease throughout the workplace and reduce the number of exposed employees. A sickness monitoring device 116 may be used to determine if an employee is exhibiting symptoms of an illness. The sickness monitoring device 116 may be associated with one or more sniffer devices 108 whose encompassed range includes sickness device 116 and/or may be associated with one or more external devices 110 capable of detecting an employee's identity. In some embodiments, the sickness monitoring device 116 is a thermometer monitor, such as an IR sensor, that measures an employee's temperature. Contact tracing server 200, memory 204, input/output circuitry 206, sickness detection circuitry 206 and the like may store an acceptable temperature range as configured and set by an authorized individual. Sickness detection circuitry 216 may receive temperature measurements from sickness monitoring device 116 and compare said measurements to the configured acceptable range. In the event a measured temperature is determined to be above or below the configured temperature range, sickness detection circuitry may generate an alert. This alert may be sent to one or more configured users via input/output circuitry 206 and/or communications circuitry 208. Said alert may include the time, location, temperature, and in some instances, identity of one or more employees and/or one or more mobile device IDs in the area. As such, proactive action may be taken to reduce the likelihood that the infected employee spreads the disease to other employees.

In some embodiments, sickness monitoring device 116 includes one or more microphones. The one or more microphones may monitor a known location and record surrounding auditory stimuli. In some embodiments, contact tracing server 200, memory 204, sickness detection circuitry 206, or the like may utilize machine learning techniques to recognize auditory stimuli indicative of illness. For example, a trained learning model may be generated using, for example, coughing and/or breathing sounds of both healthy and individuals, and upon detection of any cough or breathing sounds, the cough or breathing sound may be classified as healthy or sick. Coughing, sneezing, sniffling, and the like may all be recognized as indicative of illness. If two or more microphones are used, sickness detection circuitry 216 may use triangulation methods to narrow down the area in which the symptoms of illness were detected. In the event surrounding auditory stimuli is determined to be indicative of an illness, sickness detection circuitry may generate an alert. This alert may be sent to one or more configured users via input/output circuitry 206 and/or communications circuitry 208. Said alert may include the time, location, temperature, and in some instances, identity of one or more employees and/or mobile device ID in the area.

Figure 4:
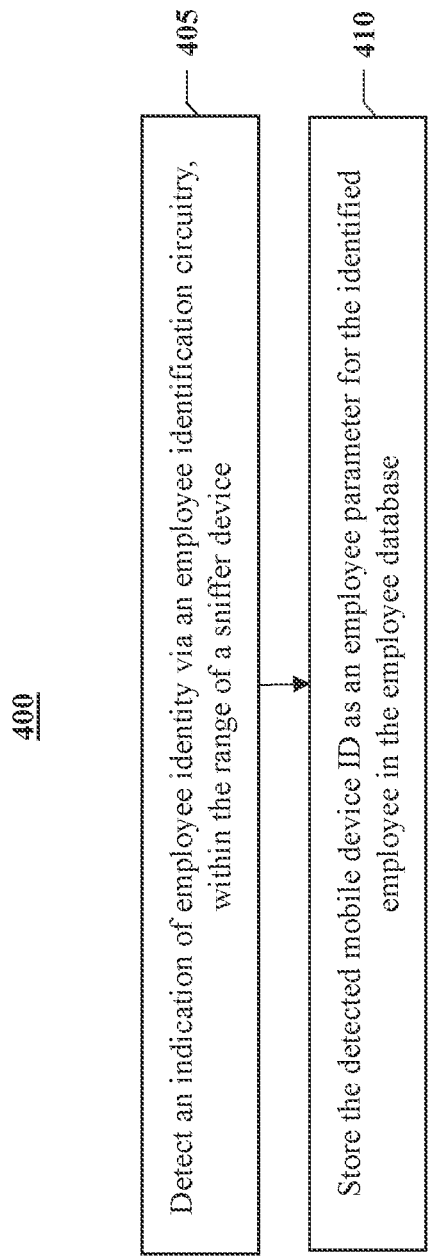
FIG. 4 illustrates an example flowchart for associating mobile devices with an employee, in accordance with some example embodiments described herein.

Turning next to FIG. 4, a flowchart 400 is shown that describes example embodiments for associating a mobile device with a particular employee. The operations illustrated in FIG. 4 may, for example, be performed by, with the assistance of, and/or under the control of an apparatus (e.g., contact tracing server 200), as described above. In this regard, performance of the operations may invoke one or more of processor 202, memory 204, input/output circuitry 206, communications circuitry 208, device ID circuitry 210, employee identification circuitry 212, location circuitry 214, and/or sickness detection circuitry 216.

In operation 405, the apparatus (e.g. contact tracing server 200) may further include means, such as the input/output circuitry 206, communications circuitry 208, employee identification circuitry 212 or the like for detecting an indication of employee identity within the range of a sniffer device 108. Indications of employee identity may be detected by one or more external devices 110. In some embodiments, an indication of employee identity may include an employee badge ID or a manually entered employee identifier received at a terminal, entrance, building, or access point. In some embodiments, an indication of employee identity may include biometric data such as facial scans, fingerprints, iris scans, retina scans, vein pattern, hair expression, bodily expression, and the like.

Employee identification circuitry 212 may access the mobile device location database 112, by way of communications circuitry 208, upon detecting an indication of employee identity. In some embodiments, employee identification circuitry 214 may be configured to associate one or more sniffer devices 108 with a specific external device 110. This may be based on the sniffer device identification data. For example, if the external device 110 is a terminal capable of detecting an indication of employee identity, one or more sniffer devices 108 whose encompassed range include the terminal may be associated with said terminal. In an instance where the terminal receives an indication of employee identity, employee identification circuitry may access the mobile device location database 112, by means of communications circuitry 208, and determine all mobile device IDs detected by the associated sniffer device 108 at the time the indication of employee identity was detected.

Thereafter, as shown in operation 410, the apparatus (e.g., contact tracing server 200) includes means, such as processor 202, memory 204, communications circuitry 208, location circuitry 214, or the like, to store the detected mobile device ID information as an employee parameter for the identified employee in the employee database 114. Employee identification circuitry 212 may access the employee database 114 by means of communications circuitry 208 and identify the employee profile based on the detected indication of employee identity. For example, an employee may be identified by an associated badge ID number. Employee identification circuitry 212 may then update the identified employee's profile to include the one or more detected mobile device IDs as detected by the associated sniffer device. Effectively, the employee profile is updated to reflect mobile devices associated with said employee.

Figure 5:
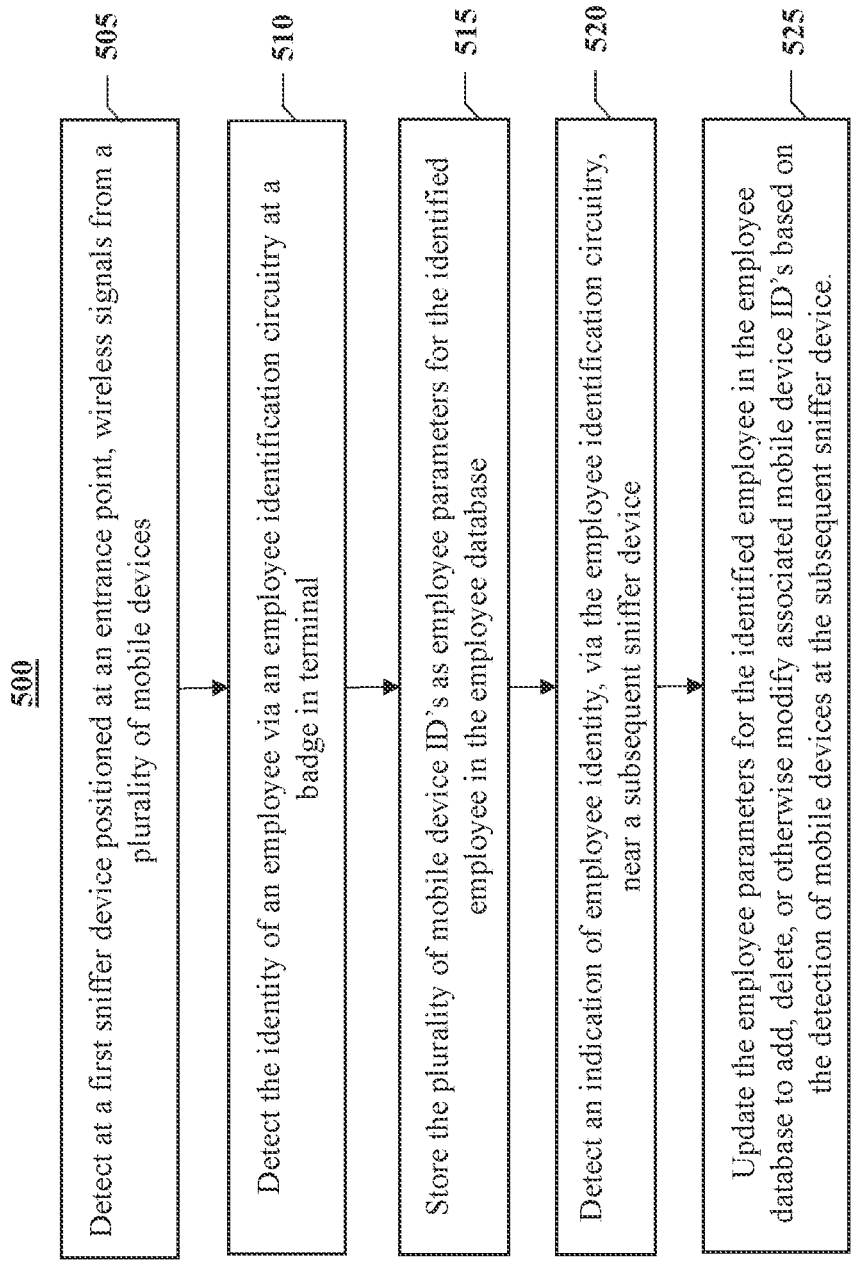
FIG. 5 illustrates an example flowchart for updating associated devices corresponding to an employee, in accordance with some example embodiments described herein.

Turning next to FIG. 5, a flowchart 500 is shown that describes example embodiments for updating associated devices with an employee. The operations illustrated in FIG. 5 may, for example, be performed by, with the assistance of, and/or under the control of an apparatus (e.g., contact tracing server 200), as described above. In this regard, performance of the operations may invoke one or more of processor 202, memory 204, input/output circuitry 206, communications circuitry 208, device ID circuitry 210, employee identification circuitry 212, location circuitry 214, and/or sickness detection circuitry 216.

In operation 505, a first sniffer device 108 may detect wireless signals from a plurality of mobile devices 106. In some embodiments, the first sniffer device is positioned near the entrance of a building such that the plurality of mobile devices are detected immediately upon entry. Similarly as in operation 310, processor 202, memory 204, communications circuitry 208, device ID circuitry 210, or the like, may generate a unique mobile ID for each mobile device of the plurality of mobile devices. Alternatively, the mobile device ID circuitry may determine a mobile device already has an assigned a mobile device ID and return the assigned mobile device ID.

In any case, the location circuitry 214 may record at least the mobile device ID for the plurality of mobile devices 106, identification data of the sniffer device that detected the wireless signals, and a detection time at which the wireless signal was detected for each of the mobile devices of the plurality of mobile devices. Using communications circuitry 208, this recorded data can be stored in the mobile device location database 112 for each respective mobile device ID.

Thereafter, as shown in operation 510, the apparatus (e.g., contact tracing server 200 and/or external device 110) includes means, such as processor 202, memory 204, input/output circuitry 206, communications circuitry 208, employee identification circuitry 212, or the like, to detect the identity of an employee, for example, at a terminal, entrance, building or area access point. In some embodiments, the terminal may be configured to detect an external device, such as a badge, to determine an identity of the employee, for example, when the employee enters, for example, by "swiping in" clocking in", etc. or via RFID. In some embodiments, the terminal may receive an employee-entered pin, code, password, etc. The terminal may be configured for face and/or voice detection and thus determine the identity of the employee upon detecting a face and/or voice of the employee. Employee identification circuitry 212 may receive this employee information by means of input/output circuitry 206 and/or communications circuitry 208. The employee identification circuitry 212 may then access the employee database 114 via communications circuitry 208 and use the received employee identification information to identify the employee profile matching the employee identification information.

Thereafter, as shown in operation 515, the apparatus (e.g., contact tracing server 200) includes means, such as processor 202, memory 204, communications circuitry 208, employee identification circuitry 212, or the like, to store the plurality of mobile device IDs as employee parameters for the identified employee in the employee database 114. Employee identification circuitry 212 may access the mobile device location database 112, by means of communication circuitry 208, to identify the plurality of mobile device IDs identified by the sniffer device associated with the terminal at the time the employee badged in. Employee identification circuitry 212 may then store the identified mobile device IDs in the identified employee's profile in the employee database 114 by way of communications circuitry 208.

Thereafter, as shown in operation 520, the apparatus (e.g., contact tracing server 200 and/or external device 110) includes means, such as processor 202, memory 204, input/output circuitry 206, communications circuitry 208, employee identification circuitry 212, or the like, to detect an indication of employee identity near a subsequent sniffer device. In some embodiments, the indication of employee identity may be detected via an external device 110, such as a terminal configured for face and/or voice detection. Said terminal may also be configured to detect employee biometric data, such as a fingerprint scan, and subsequently match said data to an employee profile in the employee database 114 via communication circuitry 208.

In some embodiments, external devices 110 may be positioned such that they are capable of detecting indications of employee identity at different and/or separate sniffer devices 108. External devices 110 may also be positioned such that they are in areas of high-traffic, such that the majority of employees interact with or pass by said external device. This is advantageous to broadly detect the majority of employees and assigning associated mobile devices to them, such that the majority of employees and their associated mobile devices are known. Additionally or alternatively, external devices 110 may be positioned in areas of low traffic such that only a few employees pass through the area. This may be advantageous when trying to more accurately associate an employee with one or more mobile devices 106.

Thereafter, as shown in operation 525, the apparatus (e.g., contact tracing server 200 and/or external device 110) includes means, such as processor 202, memory 204, input/output circuitry 206, communications circuitry 208, employee identification circuitry 212, or the like, to update the employee parameters for the identified employee in the employee database 114 to add, delete, or otherwise modify associated mobile device IDs based on the detection of mobile devices at the subsequent sniffer device 108. In instances where the subsequent sniffer device 108 no longer detects a particular mobile device ID, employee identification circuitry 212 may delete this mobile device ID as an employee parameter in employee profile of the employee database 114. If a subsequent sniffer device 108 detects a new mobile device ID or a wireless signal from a mobile device 106 without an assigned mobile device ID, the employee identification circuitry 212 may associate the mobile device ID or newly generated mobile device ID with the employee in the employee database 114.

In some embodiments, each mobile device ID may have an associated probability in the employee database 114 indicating the likelihood that a particular mobile device ID is associated with a particular employee. The associated probability may increase for each instance when the mobile device ID is detected with a particular employee. Similarly, the associated probability may decrease for each instance when the mobile device ID is not detected with a particular employee. In the event an employee is detected without a mobile device ID, the mobile device ID may not automatically be removed as a parameter from the employee profile. Instead, the associated probability may decrease. Additionally or alternatively, the associated probability for a particular mobile device ID associated with an employee may not decrease unless said mobile device ID is detected as associated with different employee. This is useful when an employee leaves a particular mobile device behind, but the mobile device does in fact belong to said employee.

In some embodiments, employees may be given a company mobile device. In this instance, the mobile device ID may be configured by an authorized user, by means of input/output circuitry 206, such that is associated with an employee in the employee database 114 and has an associated probability of one-hundred percent. In the event an employee receives a new mobile device or returns a mobile device, an authorized user may manually update the employee's profile in the employee database 114 to reflect said changes.

In some embodiments, visitors may be given temporary mobile devices such that their location is known during their visit such that they are effectively treated as an employee. Each temporary mobile device may have a configured mobile device ID and be associated with a visitor for the duration of their visit. Memory 204 may store at least the temporary device ID, visit time and date, as well as the name of the visitor. In this way, any individual maybe tracked throughout the building, thereby providing a comprehensive contact tracing method.

Figure 6:
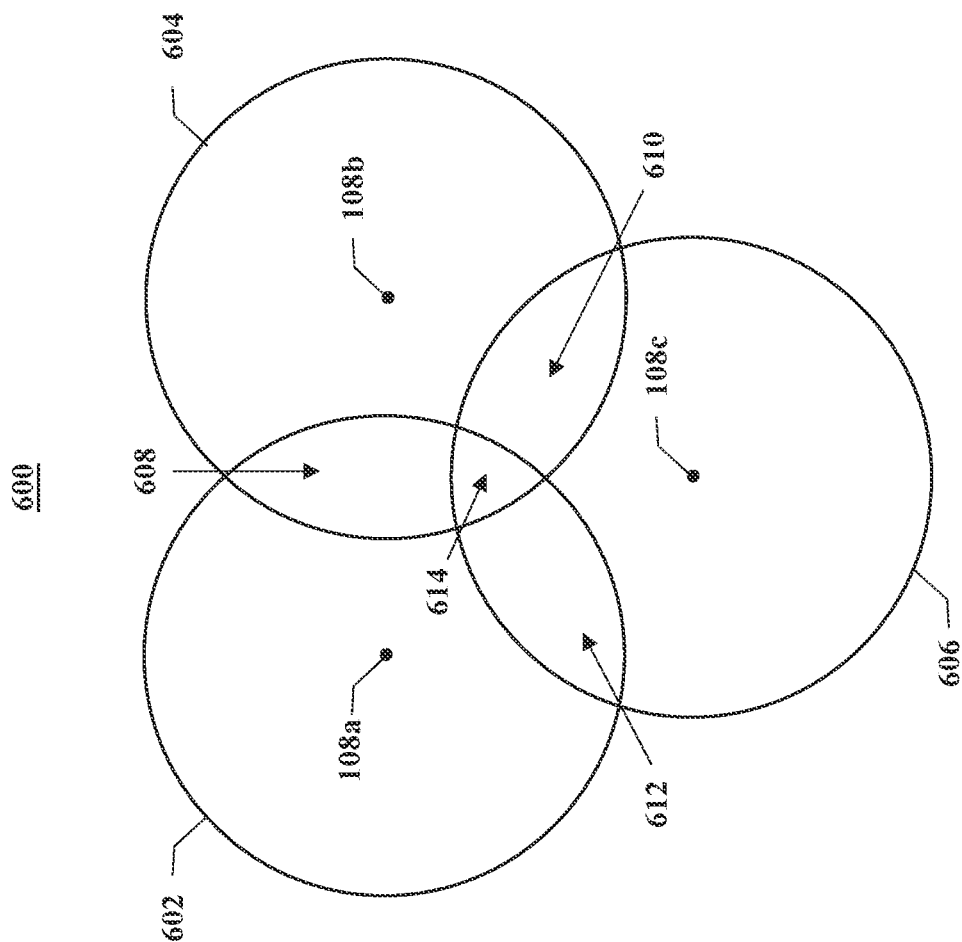
FIG. 6 illustrates an example of sniffer device grid in accordance with some example embodiments described herein.

Turning next to FIG. 6, an example of a sniffer grid is shown. The sniffer grid may include any number of sniffer devices 108 but in this example, three representative sniffer devices are shown as 108a, 108b, and 108c. The configuration of the sniffer devices is purely exemplary and any configuration with any number of sniffer devices may be contemplated.

A sniffer grid system 600 may include sniffer devices 108a, 108b, and 108c. Each sniffer device may have an associated range that it encompasses. These encompassed ranges are shown as 602, 604, and 606 for sniffer devices 108a, 108b, and 108c, respectively. Although encompassed ranges 602, 604, and 606 are shown to be relatively the same diameter, any encompassed range size and/or diameter may be contemplated.

In some embodiments, sniffer device 108a, 108b, and 108c may be placed such that their encompassed ranges overlap. These overlap areas are represented as area 608 between sniffer 108*a* and 108*b*, area 610 between sniffer 108*b* and 108*c*, area 612 between sniffer 108*c* and 108*a*, and area 614 shared by sniffer devices 108*a*, 108*b*, and 108. These areas of overlap are useful for determining a more precise and accurate position of a mobile device 106. For example, if the mobile device 106 is positioned in the area of only 602 such that it is detected only by sniffer device 108*a*, it may be difficult to accurately determine the location of the mobile device. Alternatively, if mobile device 106 is positioned in area 608 such that it is co-detected by sniffer device 108*a* and 108*b*, the encompassed area is much smaller and therefore the location of the mobile device 106 is able to be more accurately determined. Co-detections are particularly useful when attempting to triangulate a mobile device 106.

Figure 7:
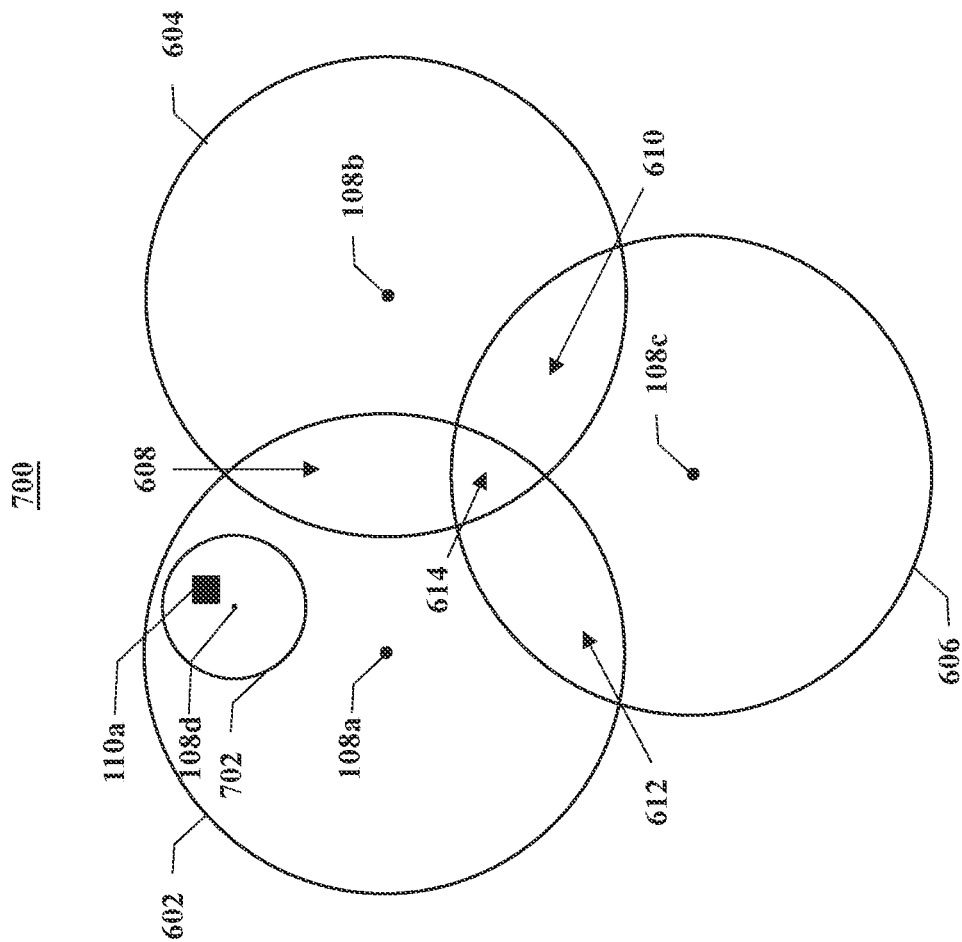
FIG. 7 illustrates an example of an alternative sniffer device grid in accordance with some example embodiments described herein.

FIG. 7 shows an alternative sniffer grid 700 configuration setup. In this example, a new sniffer device, 108*d*, is added along with a corresponding encompassed area of 702. The encompassed range 702 corresponding to sniffer device 108*d* is significantly smaller than encompassed ranges 602, 604, and 606. In this way, the location of mobile devices 106 positioned within encompassed area 702 are more accurately determined. In some embodiments, a sniffer device 106 with a small encompassed range such as sniffer device 108*d*, may strategically be placed such that they encompass places of interest, such as where an indication of employee identity may be determined. For example, 110*a* in FIG. 7 may be a terminal capable of detecting indications of employee identity that employees are required to visit prior to entering the workplace. In this way, the small encompassed area 702 which corresponds to the terminal 110*a* may more accurately associate mobile devices belonging to an employee to the correct employee and minimize erroneous associations.

Furthermore, while encompassed ranges involving co-detection of sniffer devices and/or small encompassed areas provide improved accuracy for mobile devices 106 located within said encompassed ranges, it is also beneficial for large encompassed areas. For example, if a mobile device 106 is only detected by sniffer device 108*a*, overlapping encompassed areas 702, 608, 612, and 614 may be eliminated from consideration. As such, the encompassed area of sniffer device 108*a* also experiences improved accuracy when determining the location of mobile device 106.

Each sniffer device 108 may be assigned a sniffer device ID and contact tracing server 200, processor 202, memory 204, and the like may store and reference the location of each sniffer device. The location of each sniffer device may be known relative to other sniffer devices in the same sniffer grid. Additionally, when a sniffer device is added, removed, or otherwise modified, an authorized user may update the sniffer grid in memory 204 by means of input/output circuitry 206. As such, a current and up to date sniffer grid is known.

As described above, various technical challenges are surmounted via technical solutions contemplated herein. For instance, tracing an employee's mobile device via one or more sniffer devices negates the need for an employee to download an application onto their mobile device. This allows the employee to conserve processing resources on their mobile device and frees storage in the mobile device's memory. Additionally, an employee's whereabouts and interactions may be tracked in a much more reliable way by passively tracing associated mobile devices. Furthermore, employee's may be monitored for exhibiting symptoms of an illness such that they may proactively be intercepted, and action may be taken, thereby reducing the likelihood of infecting other employees.

FIGS. 3-5 thus illustrate flowcharts describing the operation of apparatuses methods, and computer program products according to example embodiments contemplated herein. It will be understood that each flowchart block, and combinations of flowchart blocks, may be implemented by various means, such as hardware, firmware, processor, circuitry, and/or other devices associated with execution of software including one or more computer program instructions. For example, one or more of the operations described above may be implemented by an apparatus executing computer program instructions. In this regard, the computer program instructions may be stored by a memory 204 of the contact tracing server 200 and executed by a processor 202 of the contact tracing server 200. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture, the execution of which implements the functions specified in the flowchart blocks. The computer program instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the flowchart blocks.

The flowchart blocks support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware with computer instructions.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims.

Although specific terms are employed herein, they are used in a generic and descriptive sense only and not for purposes of limitation.

What is claimed is:

1. An apparatus for tracking sick employees, the apparatus comprising:
   one or more sniffer devices configured to detect a plurality of wireless signals, wherein each wireless signal of the plurality of wireless signals comprises respective mobile device identification data representative of a respective mobile device;
   device ID circuitry configured to:
   generate, for each wireless signal of the plurality of wireless signals, a respective unique mobile device ID separate from existing identification data included in the respective mobile device identification data, and
   record, for each wireless signal of the plurality of wireless signals, the respective mobile device identification data comprising the respective unique mobile device ID, identification data representative of the one or more sniffer devices; and
   employee identity circuitry configured to:
   detect an employee identity indication representative of an employee, associate the employee identity indication with the plurality of wireless signals, and record employee parameters associated with the employee comprising an association of the employee identity indication, at least in part, with each of the respective unique mobile device ID for each wireless signal of the plurality of wireless signals,
   wherein the one or more sniffer devices are further configured to detect a subset of wireless signals of the plurality of wireless signals at a subsequent sniffer device,
   wherein the employee identity circuitry is further configured to detect the employee identity indication representative of the employee near the subsequent sniffer device and update the employee parameters associated with the employee by deleting each of the respective unique mobile device IDs not associated with the subset of wireless signals of the plurality of wireless signals from among a plurality of unique mobile IDs stored in the employee parameters associated with the employee.

2. The apparatus of claim 1, wherein a sniffer device of the one or more sniffer devices comprises one or more of a Wi-Fi access point, Bluetooth scanner, or wireless access point.

3. The apparatus of claim 1, wherein the employee identity circuitry is further configured to detect an employee identity based on respective employee parameters from an employee database.

4. The apparatus of claim 1, further comprising location circuitry configured to determine a location of a mobile device using co-detections from a sniffer device of the one or more sniffer devices and one or more additional sniffer devices of the one or more sniffer devices.

5. The apparatus of claim 4, wherein the location circuitry is further configured to update employee parameters of an identified employee to add, delete, or otherwise modify mobile device IDs based on employee identification and mobile device detection at subsequent sniffer devices.

6. The apparatus of claim 1, further comprising sickness detection circuitry configured to:
   detect one or more indications of employee exhibiting symptoms of a sickness; and
   generate an alert in response to detecting a sick employee.

7. The apparatus of claim 1, wherein a sniffer device of the one or more sniffer devices is positioned at an entrance point of a building, and wherein the sniffer device is associated with a range that encompasses, at least in part, an employee identification terminal or an access point to the employee identification terminal.

8. A method for tracking sick employees using one or more sniffer devices, the method comprising:
   detecting, by the one or more sniffer devices, a plurality of wireless signals, wherein each wireless signal of the plurality of wireless signals comprises respective mobile device identification data representative of a respective mobile device;
   generating, for each wireless signal of the plurality of wireless signals by device ID circuitry, a respective unique mobile device ID separate from existing identification data included in the respective mobile device identification data;
   recording, for each wireless signal of the plurality of wireless signals by the device ID circuitry, the respective mobile device identification data comprising the respective unique mobile device ID, identification data representative of the one or more sniffer devices;
   detecting, by employee identity circuitry, an employee identity indication representative of an employee;
   associating, by the employee identity circuitry, the employee identity indication with the plurality of wireless signals;
   recording, by the employee identity circuitry, employee parameters associated with the employee comprising an association of the employee identity indication, at least in part, with each of the respective unique mobile device ID for each wireless signal of the plurality of wireless signals; and
   detecting, by the one or more sniffer devices, a subset of wireless signals of the plurality of wireless signals at a subsequent sniffer device;
   detect the employee identity indication representative of the employee near the subsequent sniffer device; and
   updating, by the employee identity circuitry, the employee parameters associated with the employee by deleting each of the respective unique mobile device IDs not associated with the subset of wireless signals of the plurality of wireless signals from among a plurality of unique mobile IDs stored in the employee parameters associated with the employee.

9. The method of claim 8, wherein a sniffer device of the one or more sniffer devices comprises one or more of a Wi-Fi access point, Bluetooth scanner, or wireless access point.

10. The method of claim 8, further comprising detecting, by the employee identity circuitry, an employee identity based on respective employee parameters from an employee database.

11. The method of claim 8, further comprising determining, by location circuitry, a location of a mobile device using co-detections from a sniffer device of the one or more sniffer devices and one or more additional sniffer devices of the one or more sniffer devices.

12. The method of claim 11, further comprising updating, by the employee identity circuitry, the employee parameters of an identified employee to add, delete, or otherwise modify mobile device IDs based on employee identification and mobile device detection at subsequent sniffer devices.

13. The method of claim 8, further comprising:
    detecting, by sickness detection circuitry, one or more indications of employee exhibiting symptoms of a sickness; and
    generating, by the sickness detection circuitry, an alert in response to detecting a sick employee.

14. The method of claim 8, wherein a sniffer device of the one or more sniffer devices is positioned at an entrance point of a building, and wherein the sniffer device is associated with a range that encompasses, at least in part, an employee identification terminal or an access point to the employee identification terminal.

15. A computer program product for tracking sick employees using one or more sniffer devices, the computer program product comprising at least one non-transitory computer-readable storage medium storing software instructions that, when executed, cause an apparatus to:
    detect a plurality of wireless signals, wherein each wireless signal of the plurality of wireless signals comprises respective mobile device identification data representative of a respective mobile device;
    generate, for each wireless signal of the plurality of wireless signals, a respective unique mobile device ID separate from existing identification data included in the respective mobile device identification data;
    record, for each wireless signal of the plurality of wireless signals, the respective mobile device identification data comprising the respective unique mobile device ID, identification data representative of the one or more sniffer devices;
    detect an employee identity indication representative of an employee;
    associate the employee identity indication with the plurality of wireless signals;
    record employee parameters associated with the employee comprising an association of the employee identity indication, at least in part, with each of the respective unique mobile device ID for each wireless signal of the plurality of wireless signals; and
    detect a subset of wireless signals of the plurality of wireless signals at a subsequent sniffer device;
    detect the employee identity indication representative of the employee near the subsequent sniffer device; and
    update the employee parameters associated with the employee by deleting each of the respective unique mobile device IDs not associated with the subset of wireless signals of the plurality of wireless signals from among a plurality of unique mobile IDs stored in the employee parameters associated with the employee.

16. The computer program product of claim 15, wherein the software instructions, when executed, further cause the apparatus to receive one or more of an employee badge number, pin code, password, or biometric data for the employee.

17. The computer program product of claim 15, wherein the software instructions, when executed, further cause the apparatus to:
    detect an employee identity based on respective employee parameters from an employee database; and
    update the employee parameters of an identified employee to add, delete, or otherwise modify mobile device IDs based on employee identification and mobile device detection at subsequent sniffer devices.

18. The computer program product of claim 15, wherein the software instructions, when executed, further cause the apparatus to determine a location of a mobile device using co-detections from a sniffer device of the one or more sniffer devices and one or more additional sniffer devices of the one or more sniffer devices.

19. The computer program product of claim 15, wherein the software instructions, when executed, further cause the apparatus to:
    detect one or more indications of employee exhibiting symptoms of a sickness; and
    generate an alert in response to detecting a sick employee.

20. The computer program product of claim 15, wherein the software instructions, when executed, further cause the apparatus to query an employee database based on one or more of a target unique mobile device ID, a proximate distance to another employee, a proximate distance to a sniffer device, a time period, a location, an employee badge number, pin code, password, or biometric data matching data.

* * * * *